(12) United States Patent
Aitken et al.

(10) Patent No.: US 9,241,889 B2
(45) Date of Patent: Jan. 26, 2016

(54) ORAL COMPOSITIONS COMPRISING SODIUM DODECYLBENZENE SULFONATE

(75) Inventors: Gail Cameron Aitken, Weybridge (GB); David Raymond Churchley, Weybridge (GB)

(73) Assignee: Glaxo Group Limited, Brentford, Middlesex (GB)

( * ) Notice: Subject to any disclaimer, the term of this patent is extended or adjusted under 35 U.S.C. 154(b) by 190 days.

(21) Appl. No.: 13/635,714

(22) PCT Filed: Mar. 22, 2011

(86) PCT No.: PCT/EP2011/054291
§ 371 (c)(1),
(2), (4) Date: Sep. 18, 2012

(87) PCT Pub. No.: WO2011/117216
PCT Pub. Date: Sep. 29, 2011

(65) Prior Publication Data
US 2013/0078198 A1    Mar. 28, 2013

(30) Foreign Application Priority Data

Mar. 24, 2010   (GB) .................................. 1004981.5

(51) Int. Cl.
*A61Q 11/00* (2006.01)
*A61K 8/27* (2006.01)
*A61K 8/46* (2006.01)
*A61K 8/34* (2006.01)

(52) U.S. Cl.
CPC . *A61K 8/466* (2013.01); *A61K 8/27* (2013.01); *A61K 8/347* (2013.01); *A61Q 11/00* (2013.01)

(58) Field of Classification Search
USPC .......................... 424/49, 56, 401, 641; 562/91
See application file for complete search history.

(56) References Cited

U.S. PATENT DOCUMENTS 4,656,031 A *    4/1987  Lane et al. ...................... 424/49
2009/0208543 A1 *  8/2009  Nathoo .......................... 424/401

FOREIGN PATENT DOCUMENTS

GB          1 290 627       *  9/1972

OTHER PUBLICATIONS

Peterson, Family Gentle Dental Care, pp. 1-6, Feb. 6, 2008.*

* cited by examiner

*Primary Examiner* — Lezah Roberts
(74) *Attorney, Agent, or Firm* — Nora L. Stein; Theodore R. Furman

(57) ABSTRACT

This invention relates to the use of sodium dodecylbenzene sulphonate (SDDBS) for helping to prevent or remove surface deposited stains from natural teeth and dental prostheses and oral care compositions comprising SDDBS for such use.

3 Claims, 5 Drawing Sheets

ORAL COMPOSITIONS COMPRISING SODIUM DODECYLBENZENE SULFONATE

FIELD OF THE INVENTION

This invention relates to the use of sodium dodecylbenzene sulphonate (SDDBS) for combating (ie helping to prevent or remove) surface deposited stains from natural teeth and dental prostheses and oral care compositions comprising SDDBS for such use. Suitable compositions include mouthwash and dentifrice compositions.

BACKGROUND OF THE INVENTION

Several factors contribute to tooth discoloration but the three main factors are believed to be: i) formation of plaque and tartar matrices on the tooth surface which then entraps stains, ii) ingestion of certain drugs during tooth formation, and iii) discoloration due to oral cavity traumatization following which blood break-down products seep into the mineralized area of the teeth during enamel formation. This invention is primarily concerned with the first factor or cause of tooth discoloration, that is the natural stain which accumulates on teeth.

Over-the-counter teeth whitening preparations have been developed to address the cosmetic preference of many to restore luster to tooth enamel discolored by surface entrapped materials. While all mouthwash and dentifrice compositions contain some cleaning and polishing agents, some tooth surface deposits may become intractable and not fully removed by these agents under normal use conditions. Also these preparations may not be formulated with the amount or type of agent required to fully remove the amount of stains and discoloration which build up due to excessive exposure to the staining agent. For example, smokers often develop discolored enamel because the tars and particulate in exhaled cigarette smoke collect on the teeth. And a number of comestibles can stain or discolor tooth enamel, tea being one example of a beverage where the tannins in the tea deposit on the tooth enamel. Some medicinal agents may cause staining or discoloration via entrapment, though this is not a usual common cause of this type of staining.

Three approaches to enamel whitening are currently in general use. They are based on using abrasives, employ oxidizing agents or utilize a hydrolytic entity to break down the staining material, e.g. enzyme-based products.

SDDBS is an anionic surfactant that is used in many oral and personal care products.

The present invention is based upon the discovery that SDDBS has anti-stain activity. In particular it has been found that SDDBS inhibits the formation of stain through its ability to prevent the uptake of dietary stain onto model surfaces. In addition to this SDDBS has been shown to remove staining in-vitro.

SUMMARY OF THE INVENTION

Accordingly, in a first aspect, the present invention provides an oral care composition for use in combating (ie helping to prevent or remove) stain from a dental surface (such as the surface of natural teeth or the surface of dental prostheses) which composition comprises SDDBS.

In a second aspect, the present invention provides the use of SDDBS in the manufacture of an oral care composition for combating stain from a dental surface.

In a third aspect, the present invention provides a method for combating stain from a dental surface, said method comprising applying an oral care composition comprising an effective amount of SDDBS to the dental surface.

DETAILED DESCRIPTION OF THE INVENTION

Figure 1:
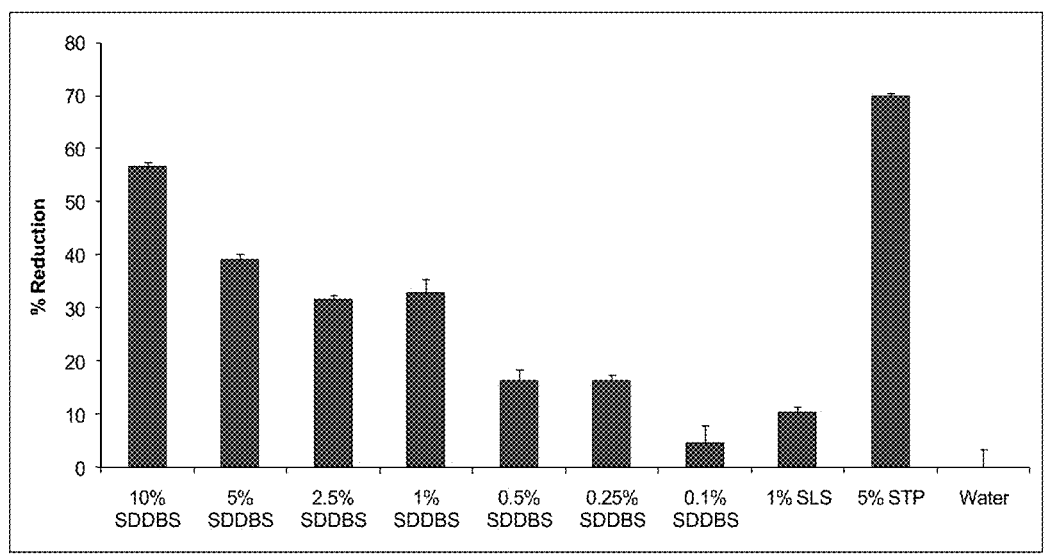
FIG. 1. is a graph depicting stain prevention dose response for SDDBS tested at over a concentration range between 0.1%-10% in the HASP model (n=8).

Suitably the SDDBS is present in an amount from 0.1% to 10.0%, for example from 0.2% to 5.0% or more suitably 0.25% to 2.0% by weight of the total composition.

SDDBS for the present invention is available from the Pilot Chemical Company, 2744 East Kemper Rd. Cincinnati, Ohio 45241 under the trade name Calsoft F90.

Oral care compositions of the present invention may comprise one or more active agents conventionally used in oral healthcare compositions, for example, a fluoride source, a desensitising agent, an anti-plaque agent; an anti-calculus agent, an oral malodour agent, an anti-inflammatory agent or a mixture of at least two thereof. Such agents may be included at levels to provide the desired therapeutic effect.

Suitably the composition of the present invention further comprises a source of zinc ions. Zinc ions have antibacterial properties useful in helping to prevent, inhibit and/or treat oral health conditions caused or exacerbated by the presence of bacteria in the oral cavity, including periodontal (gum) disease, dental caries, halitosis, dental plaque and dental calculus.

Suitably the source of zinc ions, as defined as the zinc portion of a corresponding salt, is present in an amount from 0.01% to 2.50%, for example from 0.04% to 0.70% by weight of the total composition.

Suitably the source of zinc ions is a zinc salt such as zinc chloride, zinc citrate, zinc acetate, zinc sulphate, zinc gluconate, zinc salicylate, zinc lactate, zinc maleate, zinc malate, zinc tartrate, zinc carbonate, zinc phosphate, zinc oxide or zinc sulphate. Additional zinc salts are described in U.S. Pat. No. 4,022,880 (Vinson et al).

A preferred zinc salt is zinc chloride.

Suitably the composition of the present invention further comprises 4-isopropyl-3-methylphenol (IPMP). IPMP has antibacterial and anti-inflammatory activities useful in helping to prevent, inhibit and/or treat oral health conditions caused or exacerbated by the presence of bacteria in the oral cavity.

Suitably the IPMP is present in an amount from 0.005% to 1.00%, for example from 0.01% to 0.20% or 0.05% to 0.10% by weight of the total composition.

Oral care compositions comprising the combination of IPMP, a zinc salt and SDDBS exhibit enhanced antibacterial activtivity coupled together with useful anti-inflammatory activity and anti-staining benefits.

Oral care compositions of the present invention are typically formulated in the form of toothpastes, sprays, mouthwashes, mouthrinse, gels, lozenges, chewing gums, tablets, pastilles, instant powders, oral strips, buccal patches, wound dressings and denture adhesives.

In an embodiment the composition of the present invention is a toothpaste composition, more suitably a mouthwash composition comprising an orally acceptable carrier or excipient.

Oral care compositions of the present invention will contain additional formulating agents such as abrasives, thickening agents, surfactants, humectants, flavouring agents, sweetening agents, opacifying or colouring agents, preservatives and water, selected from those conventionally used in the oral hygiene composition art for such purposes.

Suitable oral care actives and orally acceptable carriers or excipients (ie the above-noted formulating agents) are described for example in US 2007/0053849 (Procter & Gamble).

The compositions according to the present invention may be prepared by admixing the ingredients in the appropriate relative amounts in any order that is convenient and if necessary adjusting the pH to give a final desired value.

When the composition is in the form of a toothpaste, it is suitable for containing in and dispensing from a laminate tube or a pump as conventionally used in the art.

The invention will now be described by way of the following Examples and data.

Examples

1. Hydroxyapatite Stain Prevention Model (HASP)

Methodology.

A 96 well hydroxyapatite coated microtitre plate was treated with whole unstimulated human saliva (100 µl per well) at 37° C./100 rpm. After 1 hour the plate was washed to remove any unbound components and 200 µl of each test active was transferred to the plate in columns along with a positive and negative control (5% sodium tripolyphosphate, STP), and water respectively) and the plate returned to the incubator. After 10 minutes the plate was once again washed and the plate was stained by the application of 200 µl of fresh tea solution (1 teabag (PG tips)/50 ml of deionised water). After an additional 10 minutes of incubation, the tea was removed and the plate washed. Finally, the bound stain was desorbed by the application of 200 µl of 2.5M citric acid per well. After a minimum of 12 hours, 180 µl of the tea/citric acid solutions were transferred to a clean, normal (not HA coated) 96 well microtitre plate and the absorption measured 405 nm.

2. Hydroxyapatite Tea Stain Removal Model (HATSR)

Methodology

A 96 well hydroxyapatite coated microtitre plate was treated with 100 µl aliquots of tea per well (1 teabag (PG Tips)/50 ml of deionised water) and the plate incubated at 37° C./100 rpm. After 10 minutes the plate was washed with deionised water and dried at 37° C. overnight. The test actives (200 µl per well) were added into each column of the tea coated plate along with the positive and negative control (5% sodium tripolyphosphate (STP) and water respectively) and the plate returned to the incubator. After 10 minutes the plate was once again washed and the bound stain was desorbed by the application of 200 µl of 2.5M citric acid per well. After a minimum of 12 hours, 180 µl of the tea/citric acid solutions were transferred to a clean, normal (not HA coated) 96 well microtitre plate and the absorption measured 405 nm.

3.1. Solutions

All solutions were tested at pH 7

Conclusion

The results in FIG. 1 show that SDDBS prevents the uptake of dietary stain onto HASP model oral surfaces. All SDDBS concentrations were statistically superior to the water negative control with the exception of 0.1% (which was only directionally superior) but none were as effective as the positive control STP (a known anti-staining agent used in many whitening toothpastes).

Conclusion

Figure 2:
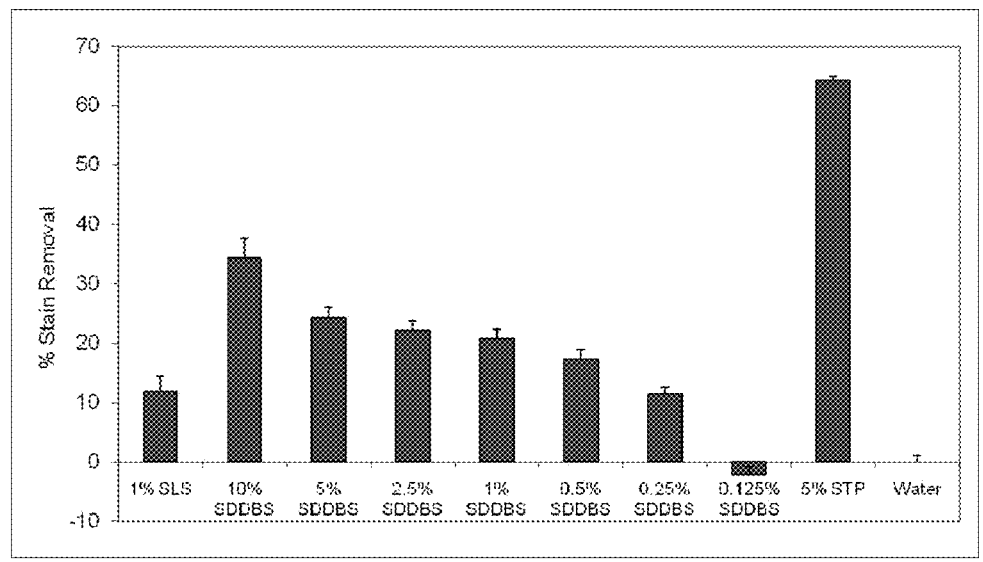
FIG. 2: is a graph depicting stain removal dose response for SDDBS tested at over a concentration range between 0.1%-10% in the HATSR model (n=8).

The results of the HATSR Model test in FIG. 2 show that SDDBS removes stain in a dose dependent manner. All SDDBS concentrations with the exception of 0.125% were statistically superior to the water negative control but none were as effective as the positive control STP (a known anti-staining agent used in many whitening toothpastes).

Conclusion

Figure 3:
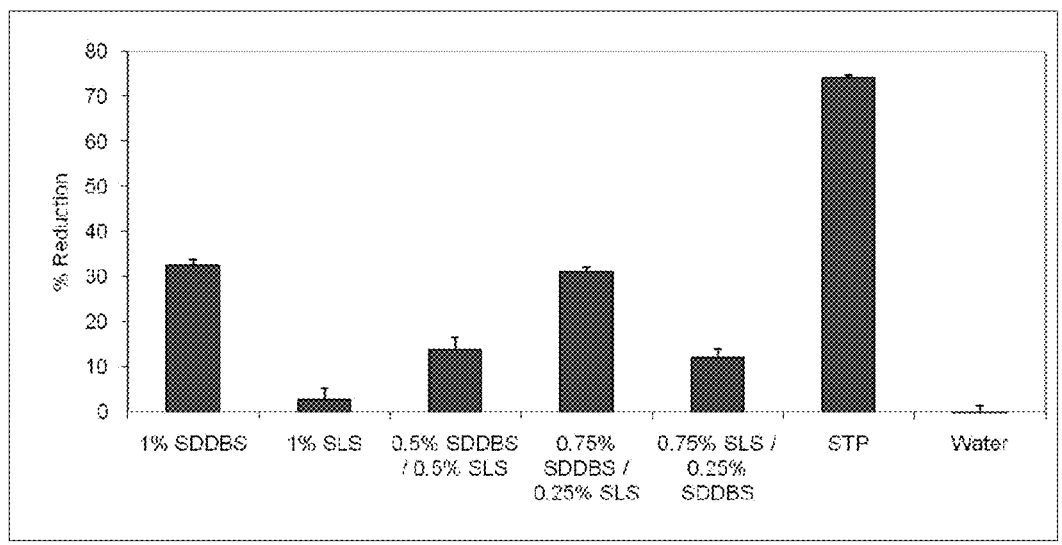
FIG. 3: is a graph depicting stain prevention data for SDDBS/SLS combinations (total surfactant level: 1%) tested in the HASP model (n=8).

The results of the HASP Model test in FIG. 3 show that SDDBS is statistically superior to sodium lauryl sulphate (SLS) at equivalent concentration.

By maintaining the surfactant concentration constant at 1%, combinations of SDDBS and SLS were shown to be less effective than 1% SDDBS but still superior to SLS alone. All treatments containing SDDBS were superior to water but not as effective as the positive control STP (a known anti-staining agent used in many whitening toothpastes).

Example Formulations

Mouthwash formulations containing SDDBS were also evaluated in the HASP (FIG. 4) and HATSR (FIG. 5) models against a number of commercially available products.

Conclusion

All 3 experimental mouthwashes (MW1, MW2 and MW3) that contain 0.5% SDDBS were shown to be statistically superior to the commercially available products at preventing the deposition of and removal of a dietary stain in vitro. Unlike the commercial products (with the exception of Listerine (Original and Total Care), these formulations do not contain cationic anti-microbial agents such as cetylpyridinium chloride (CPC) and chlorhexidine which can bind stain chromagens and increase staining.

Figure 4:
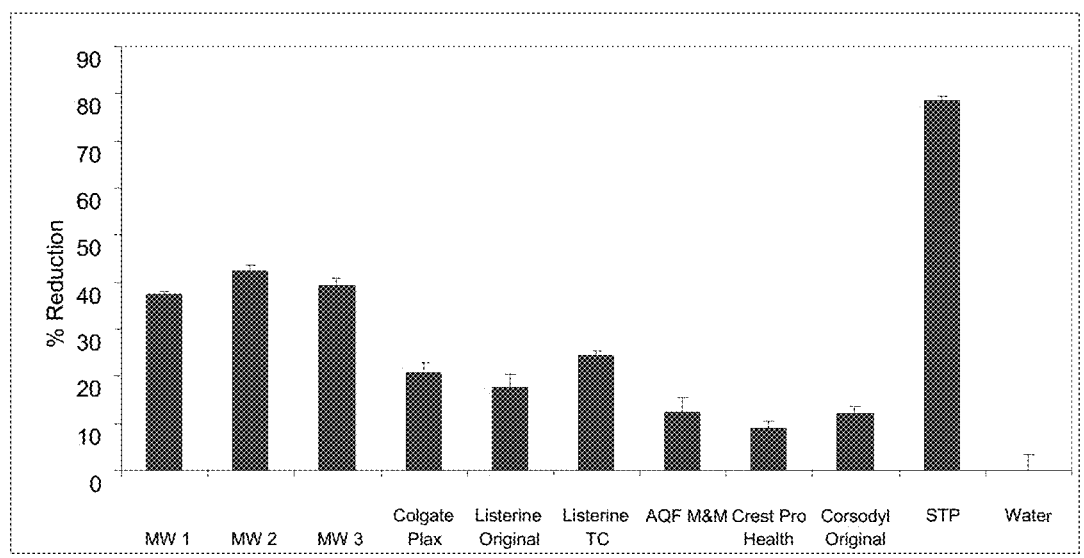
FIG. 4: is a graph depicting stain prevention data for experimental formulations containing 0.5% SDDBS vs commercially available products tested in the HASP model (n=8).
Figure 5:
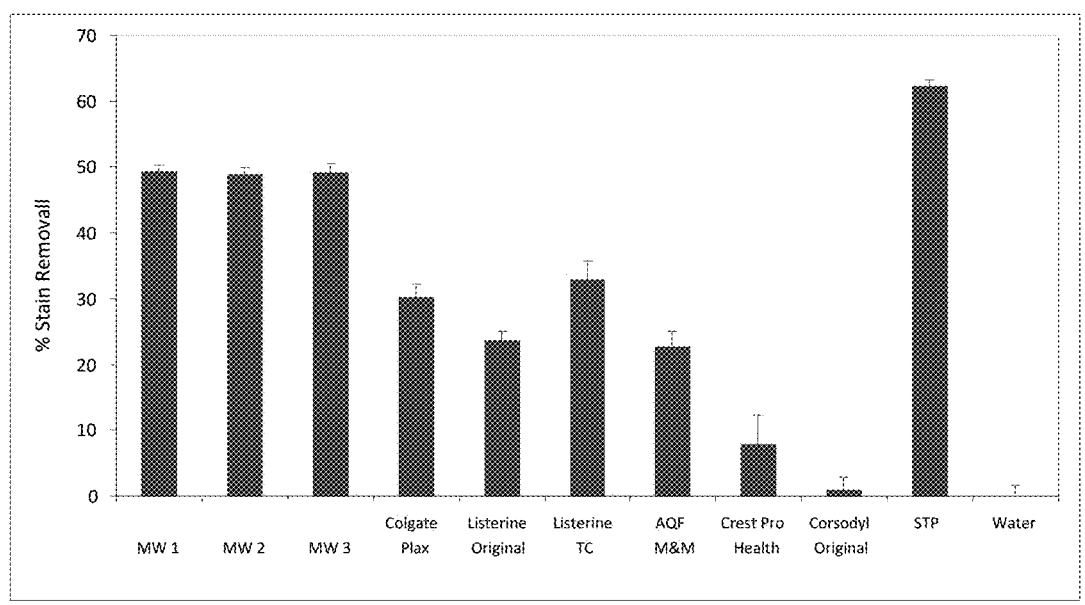
FIG. 5: is a graph depicting stain removal data for experimental formulations containing 0.5% SDDBS vs commercially available products tested in the HATSR model (n=8).

MW Example formulations 1-3 (as shown in FIGS. 4 and 5)

|  | Mouthwash Composition | | |
| --- | --- | --- | --- |
| Raw Material | MW1 % w/w | MW2 % w/w | MW3 % w/w |
| Glycerin (98%) | 10.00 | 10.00 | 10.00 |
| SDDBS | 0.50 | 0.50 | 0.50 |
| IPMP | 0.01 | 0.05 | 0.03 |
| Saccharin Sodium | 0.03 | 0.03 | 0.03 |
| Sodium Fluoride | 0.55 | 0.55 | 0.55 |
| Zinc Chloride | 0.10 | 0.10 | 0.10 |
| Bisabolol | 0.05 | 0.05 | 0.05 |
| Cremophor RH60 | 0.50 | 0.50 | 0.50 |
| Flavour | 0.25 | 0.25 | 0.25 |
| Sodium citrate tribasic dihydrate | 0.50 | 0.50 | 0.50 |
| Preservatives | 0.20 | 0.20 | 0.20 |
| Purified Water | ad 100 | ad 100 | ad 100 |

The invention claimed is:

1. A method for combating stain on a dental surface, said method comprising applying to the dental surface a composition consisting essentially of a source of zinc ions, 4-isopropyl-3-methylphenol (IPMP) and, as an active anti-stain agent, an effective amount of sodium dodecylbenzene sulfonate (SDDBS).

2. The method according to claim 1 wherein the source of zinc ions is selected from zinc chloride, zinc citrate, zinc acetate, zinc sulphate, zinc gluconate, zinc salicylate, zinc lactate, zinc malate, zinc maleate, zinc tartrate, zinc carbonate, zinc phosphate, zinc oxide or zinc sulphate.

3. The method according to claim 2 wherein the source of zinc ions is zinc chloride.

\* \* \* \* \*